United States Patent
Frick et al.

(10) Patent No.: US 11,219,764 B2
(45) Date of Patent: Jan. 11, 2022

(54) DYNAMIC ELECTRO ENHANCED PAIN CONTROL (DEEPC) DEVICE FOR DELIVERY OF ELECTRICAL PULSES TO A DESIRED BODY PART OF A MAMMAL

(71) Applicant: SCANDINAVIAN CHEMOTECH AB, Lund (SE)

(72) Inventors: Mohan Frick, Gothenburg (SE); Bertil R R Persson, Lund (SE)

(73) Assignee: Scandinavian Chemotech AB, Lund (SE)

( * ) Notice: Subject to any disclaimer, the term of this patent is extended or adjusted under 35 U.S.C. 154(b) by 0 days.

(21) Appl. No.: 16/633,327

(22) PCT Filed: Jul. 27, 2018

(86) PCT No.: PCT/EP2018/070473
§ 371 (c)(1),
(2) Date: Jan. 23, 2020

(87) PCT Pub. No.: WO2019/020809
PCT Pub. Date: Jan. 31, 2019

(65) Prior Publication Data
US 2020/0155850 A1  May 21, 2020

Related U.S. Application Data

(60) Provisional application No. 62/538,402, filed on Jul. 28, 2017.

(51) Int. Cl.
*A61N 1/36* (2006.01)
*A61N 1/04* (2006.01)

(52) U.S. Cl.
CPC ....... *A61N 1/36071* (2013.01); *A61N 1/0472* (2013.01); *A61N 1/3614* (2017.08); *A61N 1/36153* (2013.01); *A61N 1/36171* (2013.01)

(58) Field of Classification Search
CPC .............. A61N 1/36071; A61N 1/3614; A61N 1/0472; A61N 1/36153; A61N 1/36171;
(Continued)

(56) References Cited

U.S. PATENT DOCUMENTS 5,069,223 A * 12/1991 McRae ................. A61B 5/0535
600/547
5,921,982 A * 7/1999 Lesh ................... A61B 18/1492
606/41

(Continued)

FOREIGN PATENT DOCUMENTS

KR  10-2016-0145184 A  12/2016
WO  98/14238 A1  4/1998
(Continued)

OTHER PUBLICATIONS

Panagopoulos DJ, Johansson O, Carlo GL (2013) Evaluation of Specific Absorption Rate as a Dosimetric Quantity for Electromagnetic Fields Bioeffects. PLoS ONE 8(6): e62663. doi: 10.1371/journal.pone.0062663 (Year: 2013).*

(Continued)

*Primary Examiner* — Carl H Layno
*Assistant Examiner* — Manolis Pahakis
(74) *Attorney, Agent, or Firm* — Merchant & Gould P.C.

(57) ABSTRACT

A device for delivery of electrical pulses to a desired tissue of a mammal. The device comprises a pulse generating device and an electrode device connected to the pulse generating device. The pulse generating device is configured to determine conductance and phase angle values between one electrode and a reference electrode of the electrode device when the electrode device is inserted into the desired tissue and when pulses based on alternating currents having different frequencies are generated between the electrode and the reference electrode. Based on the determined con- (Continued)

ductance and phase angle values, the pulse generating device is configured to determine the type of tissue the electrode device penetrates, to determine one or more parameters of electrical pulses to be delivered to the desired tissue and to generate the electrical pulses having the determined one or more parameters.

8 Claims, 12 Drawing Sheets

(58) Field of Classification Search
CPC ... A61N 1/327; A61N 1/36031; A61N 1/0412
See application file for complete search history.

(56) References Cited

U.S. PATENT DOCUMENTS

| | | | | | |
|---|---|---|---|---|---|
| 8,728,071 | B2* | 5/2014 | Lischinsky | ........ | A61B 18/1206 606/34 |
| 2002/0077627 | A1* | 6/2002 | Johnson | ............. | A61B 18/1477 606/41 |
| 2006/0085049 | A1* | 4/2006 | Cory | ................... | A61B 5/0536 607/48 |
| 2008/0312713 | A1* | 12/2008 | Wilfley | ............. | A61B 18/1492 607/41 |
| 2009/0036794 | A1* | 2/2009 | Stubhaug | ............. | A61B 5/053 600/547 |
| 2009/0171235 | A1* | 7/2009 | Schneider | ............. | A61B 5/053 600/547 |
| 2010/0217360 | A1* | 8/2010 | Henriksson | .......... | A61N 5/0601 607/96 |
| 2010/0228240 | A1* | 9/2010 | Henriksson | .............. | A61N 1/06 606/28 |
| 2011/0004207 | A1* | 1/2011 | Wallace | ............. | A61B 17/1757 606/35 |
| 2011/0152859 | A1* | 6/2011 | Long | ................. | A61B 18/1402 606/41 |
| 2011/0306867 | A1* | 12/2011 | Gopinathan | ........... | A61B 5/064 600/407 |
| 2012/0071782 | A1* | 3/2012 | Patil | ...................... | A61B 5/064 600/547 |
| 2012/0191003 | A1* | 7/2012 | Garabedian | .......... | A61N 1/0551 600/554 |
| 2012/0221069 | A1* | 8/2012 | Rosenberg | ......... | A61N 1/36592 607/18 |
| 2012/0226200 | A1* | 9/2012 | Wagner | .............. | A61N 1/36025 601/2 |
| 2012/0323134 | A1* | 12/2012 | Cory | .................... | A61B 5/0536 600/547 |
| 2012/0323237 | A1* | 12/2012 | Paul | ................... | A61B 18/1206 606/41 |
| 2013/0023946 | A1* | 1/2013 | Valvano | ............. | A61N 1/36125 607/18 |
| 2014/0005658 | A1* | 1/2014 | Rosenbegr | ............ | A61B 18/18 606/33 |
| 2015/0025352 | A1* | 1/2015 | Caytak | ................. | A61B 5/0531 600/383 |
| 2016/0278856 | A1* | 9/2016 | Panescu | ................. | A61B 5/068 |
| 2017/0296090 | A1* | 10/2017 | Kalvoy | ................... | A61B 5/053 |
| 2019/0046104 | A1* | 2/2019 | Samani | .................. | G01R 27/26 |
| 2019/0117964 | A1* | 4/2019 | Bahrami | ................ | A61N 1/327 |
| 2020/0155850 | A1* | 5/2020 | Frick | .................... | A61N 1/0472 |

FOREIGN PATENT DOCUMENTS

| | | | | |
|---|---|---|---|---|
| WO | 99/52589 | A1 | 10/1999 | |
| WO | 00/67837 | A1 | 11/2000 | |
| WO | WO-2007078997 | A2 * | 7/2007 | ............ A61N 1/327 |
| WO | 2008/090444 | A1 | 7/2008 | |
| WO | 2009/091578 | A1 | 7/2009 | |
| WO | 2011/075485 | A2 | 6/2011 | |
| WO | 2011/094110 | A1 | 8/2011 | |
| WO | WO-2016090175 | A1 * | 6/2016 | .......... A61B 17/122 |
| WO | 2016/161201 | A2 | 10/2016 | |

OTHER PUBLICATIONS

International Search Report and Written Opinion from corresponding International Application No. PCT/EP2018/070473, dated Jan. 3, 2019.

* cited by examiner

DYNAMIC ELECTRO ENHANCED PAIN CONTROL (DEEPC) DEVICE FOR DELIVERY OF ELECTRICAL PULSES TO A DESIRED BODY PART OF A MAMMAL

This application is a National Stage Application of National Stage Application No. PCT/EP2018/070473, filed Jul. 27, 2018, which claims benefit of Ser. No. 62/538,402, filed Jul. 28, 2017 in the United States of America and which applications are incorporated herein by reference. To the extent appropriate, a claim of priority is made to each of the above disclosed applications.

TECHNICAL FIELD

Embodiments herein relate to a device, e.g. a DEEPC™ device, and to methods therein. Especially, embodiments herein relate to the delivery of electrical pulses to a desired body part of a mammal.

BACKGROUND

Pulsed electric fields applied to biological cells and tissues create transverse channels or pores in the cell membrane, a phenomenon called electro-permeabilization or electroporation. The explanation to pore formation is the reorganization of interfacial water in structures of the lipid bilayer membranes due to the pulsed applied electric fields.

Electroporation increases the probability for the migration of hydrophilic molecules through the cell membranes. Thus, molecules outside the cells move into the cytoplasm, and out of the cytoplasm migrate intracellular antigenic molecules to the extracellular space. The rate of resealing the membranes and recovery of the cells depend on the strength of the applied voltage, and the number and length of the applied electric pulses.

Most electroporation protocols for experimental, clinical, and biotechnological applications use pulses, e.g. direct current (DC) pulses, of about 1000 V/cm, with durations of at least 100 μs. But membrane permeabilization also occurs with shorter pulses with pulse-lengths, in the range of 100 ns, however, at a much higher electric field-strength.

The concept of electro-permeabilization is employed in tumour treatment by increasing the permeability of tumour cells, and thus to enhance the access of administered cytotoxic agents to solid tumours. Generally, a low dose of bleomycin, a highly toxic antibiotic agent that normally does not penetrate the tumour cell membrane, is administered either intravenously (15000-25000 International Units (IU)), or directly to the tumours (260-1000 IU/cm$^3$) before electric pulses are applied to them. However, a combination of intravenous and direct administration of the agent may be applied. By applying the electric pulses, the therapeutic effect of the chemotherapy can be enhanced.

This procedure applied clinically is usually called Electro-Chemo-Therapy (ECT), and commonly packages of 8 rectangular pulses are delivered within 2 s with a nominal electric field strength of about 1000 V/cm (that means a voltage of 1000 V applied between pin electrodes with distance of about 4-12 mm, e.g. about 8-10 mm), and with a duration of 100 μs for each pulse. In an example protocol, totally 96 electric pulses may be delivered over a number of (e.g. 12) pairs of electrodes in the applicator. The general hypothesis is that the efficacy of ECT is due to the applied voltage and the distance between the electrodes. The absorbed energy per pulse is estimated to about 500 J/kg and the current about 16 A. This seems, however, to be too detrimental to tissues, particularly in head and neck treatments. The use of a too high electric field strength and a too high current cause inflammatory response and immune suppression that limit the infiltration of killer T-cells to the treated tumour.

WO9814238A1 discloses an apparatus comprising means for ionizing radiation and a high voltage generator for generating brief voltage pulses for voltage application of electrodes included in the apparatus. The electrodes are designed to be secured at or introduced into tissue in a restricted region of a human or an animal and to form between them an electric field in the tissue. The means are provided to emit ionizing radiation to a tumour in the tissue in that region which is to be treated, while the electrodes are disposed to be placed in or at the tumour so that the electric field pass through the tumour.

WO9952589A1 discloses an apparatus comprising a voltage generator for generating brief voltage pulses for the impression of voltage on electrodes included in the apparatus, and a measurement unit, which is coupled to the electrodes. The electrodes are designed to be secured at or inserted in tissue in a restricted region of a human or an animal in order to form electric fields in the tissue between the electrodes. The measurement unit is disposed to determine the impedance between the electrodes, which is substantially determined by the electric properties of the tissue located between the electrodes. A registration and calculator device forms a control unit, which, based on the impedance determined by the measurement unit, controls the output voltage of the voltage generator such that the electric field, which is formed in the tissue, always has a predetermined value. The treatment with the electric field realizes a perforation of cell membranes in the tissue which thereby permits the passage of substances fed to the body, e.g. cytostatic or genetic material.

A drawback with previously known devices is that a too high electric field strength and a too high current may be applied to the treatment volume of the mammal causing inflammatory response and immune suppression that limit the infiltration of killer T-cells to the treated tumour.

SUMMARY

An aim of some embodiments disclosed herein is to overcome or mitigate at least some of the drawbacks with the prior art.

According to an aspect of embodiments herein, the object is achieved by a device for delivery of electrical pulses to a desired tissue of a mammal. The device comprises a pulse generating device and an electrode device connected to the pulse generating device.

The pulse generating device is configured to, by means of an impedance measuring module, determine conductance and phase angle values between one electrode of the electrode device and a reference electrode of the electrode device, when the electrode device, when in use, is inserted into a desired body part comprising the desired tissue and when pulses based on alternating currents having different frequencies are generated to the desired body part between the electrode and the reference electrode.

Further, the pulse generating device is configured to, based on the determined conductance and phase angle values, determine the type of tissue the electrode device penetrates, when the electrode device, when in use, is inserted into the desired body part.

Furthermore, the pulse generating device is configured to, based on the determined conductance and phase angle values, determine one or more parameters of electrical pulses to be delivered to the desired tissue, when the electrode device in use is arranged at the desired tissue; and to generate the electrical pulses having the determined one or more parameters.

Since the type of tissue penetrated by the electrode device and the one or more parameters of electrical pulses to be delivered to the desired tissue are determined based on the determined conductance and phase angle values, an improved control of generated electrical pulses to the desired tissue is provided.

An advantage with some embodiments disclosed herein is that a current density and/or a specific absorbed energy in a desired body part may be controlled to achieve pain relief in the desired body part and possibly also to enhance a therapeutic effect.

BRIEF DESCRIPTION OF DRAWINGS

Examples of embodiments herein will be described in more detail with reference to attached drawings in which.

DETAILED DESCRIPTION

As previously mentioned, an aim of some embodiments disclosed herein is to overcome or mitigate at least some of the drawbacks with the prior art.

Thus, an aim of some embodiments disclosed herein is to provide a pulse generating device having an improved control of the generation of electrical pulses. Thereby, by means of embodiments disclosed a current density and a specific absorbed energy in a desired body part is controlled to achieve pain relief in the desired body part and possibly also to enhance a therapeutic effect.

Another aim of some embodiments disclosed herein is to provide for an improved positioning of electrodes in a desired body part.

In the following, embodiments herein are illustrated by exemplary embodiments. It should be noted that these embodiments are not mutually exclusive. Components from one embodiment may be tacitly assumed present in another embodiment and it will be obvious to a person skilled in the art how those components may be used in the other exemplary embodiments.

It should furthermore be noted that, to anyone skilled in the art, there are several realizations of the embodiments below with principally equivalent functionality.

Embodiments disclosed herein relate to an electrode device and to a pulse generating device. The electrode device is connectable to a pulse generating device to deliver electrical pulses to a desired body part of a mammal when the electrode device is arranged at, e.g. inserted into, the desired body part. The electrode device and the pulse generating device are sometimes referred to as a device for dynamic electric enhanced pain control or as a Dynamic Electro Enhanced Pain Control (D-EEPC™ or DEEPC™) device. For example, the DEEPC device may be used to obtain pain relief in the spine of a mammal, which pain in the spine may be due to e.g. bone metastases.

Some First Exemplifying Embodiments

Figure 1:
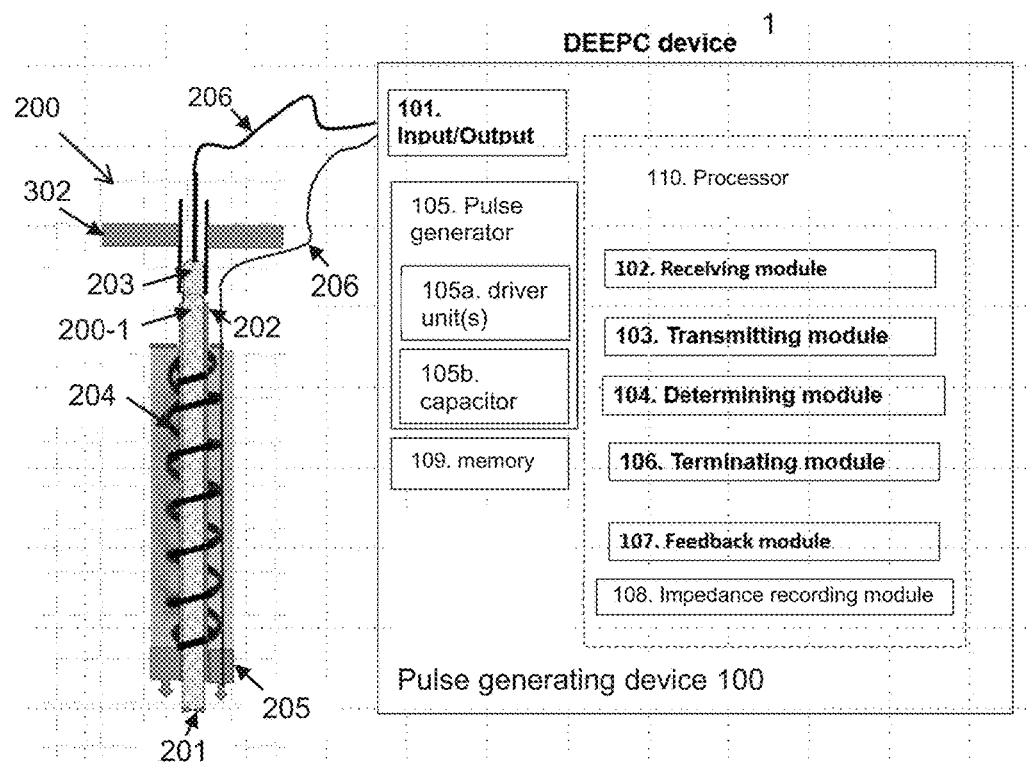
FIG. 1 schematically illustrates some first embodiments of a DEEPC device.

In some first embodiments, schematically illustrated in FIG. 1, an electrode device 200 comprises one or more needle electrodes 200-1 releasable arranged to a pulse generating device 100. The pulse generating device 100 will be described in more detail below.

The DEEPC device 1 may be an integrated treatment unit comprising one or more electrodes 200-1 connected to the pulse generating device 100. The device 1 may be configured to perform combined Electro Enhanced Chemotherapy (EECT) and Electro-Enhanced-Ablation (EEA) based on modulated AC-pulses with frequency components in the range of 1 kHz to 1000 kHz.

Figure 2:
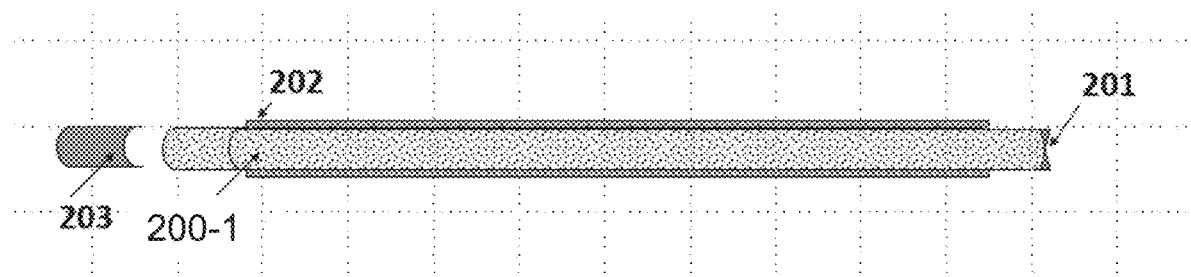
FIG. 2 schematically illustrates a longitudinal cross-section of embodiments of a first electrode device.

As illustrated in FIG. 1, the pulse generating device 100 comprises an impedance recording unit 108 and a pulse generator 105 controlled by a processor 110. FIG. 2 schematically illustrates a cross-sectional view of embodiments of an electrode 200-1. In some embodiments, the electrode 200-1 is shaped as an elongated drill comprising an elongated insulating cover 202 along its longitudinal envelope surface but not at the ends of the electrode 200-1. One of the ends of the electrode 200-1, e.g. a first end that also may be referred to as a front end, comprises a tip 201, which tip 201 may have a cut. The tip 201 is configured for penetration into the desired body part, e.g. into a vertebra of the mammal. The other end of the electrode 200-1, e.g. a second end that may be opposite to the first end, is configured to be connected to the pulse generating device 100 by means of suitable cabling 206.

Figure 3:
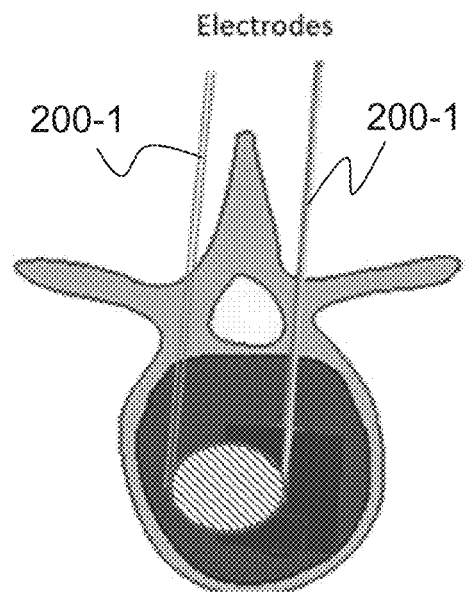
FIG. 3 schematically illustrates a first electrode device comprising two needle electrodes placed in a vertebra.

FIG. 3 schematically illustrates an electrode device 200 comprising two needle electrodes 200-1 placed in the vertebra.

Figure 4:
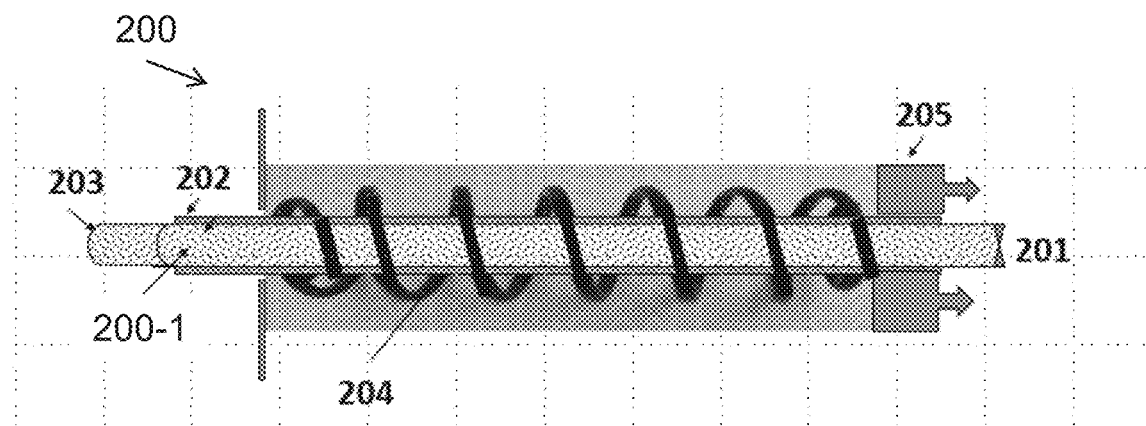
FIG. 4 schematically illustrates a longitudinal cross-section of a reference electrode surrounding a central electrode with a spring.

In order to enable impedance measurements, a reference electrode 205, is to be arranged at an entrance surface of the desired body part of the mammal. The reference electrode 205 may be a sliding reference electrode 205 surrounding the electrode 200-1 with a spring 204 and which sliding reference electrode 205 pushes against an entrance surface of the mammal, e.g. pushes against an entrance surface of the desired body part of the mammal into which desired body part the electrode 200-1 is inserted. The arrangement of the sliding electrode 205 and the central electrode 200-1 is schematically illustrated in FIG. 4.

The impedance Z is the ratio of the voltage V applied over an AC electric circuit (with resistors and capacitors), and the current I through the circuit. i.e. Z=V/I. In a DC circuit with only resistors, the impedance is equal to the resistance R, i.e. Z=R=V/I. Thus 1/R is the DC-conductance and 1/Z is the AC-conductance (also called admittance).

Impedance measurement may be performed by measuring the current between the electrode 200-1 and the reference electrode 205. The impedance between the electrode 200-1 and the reference electrode 205 will be a measure of the opposition the medium between the electrode 200-1 and the reference electrode 205 presents to the current when a voltage is applied over the electrode 200-1 and the reference electrode 205. If the electrodes 200-1, 205 are inserted into a tissue of a body part, the impedance measurement will be a measure of the opposition the tissue of the body part exerts to the current caused between the electrodes 200-1,205 when the voltage is applied to the electrodes 200-1,205. Thus, the inverse of the measured impedance 1/Z will also be a measure of the conductance, e.g. i.e. the AC conductance, of the tissue of the body part, as the conductance is a measure of the ease with which an electric current passes through the tissue.

The insertion of the electrode 200-1 into the desired body part, e.g. into the vertebra, may be done using an alternately rotating electric device. The alternately rotating electric device may be connected to the electrode device 200, e.g. to the electrode 200-1 and to the reference electrode 205, by means of a connector 203.

Alternatively, the insertion of the electrode 200-1 may be accomplished with a hand tool with a handle 302 attached to the electrode device 200, e.g. to the electrode 200-1, by means of the connector 203. With the operator's grip, the electrode 200-1 may be rotated alternately <180 degrees back and forth so that the electrode 200-1 penetrates into the desired body part, e.g. into the vertebra of the mammal, with maintained electrical contact without twisting the wiring.

Figure 5:
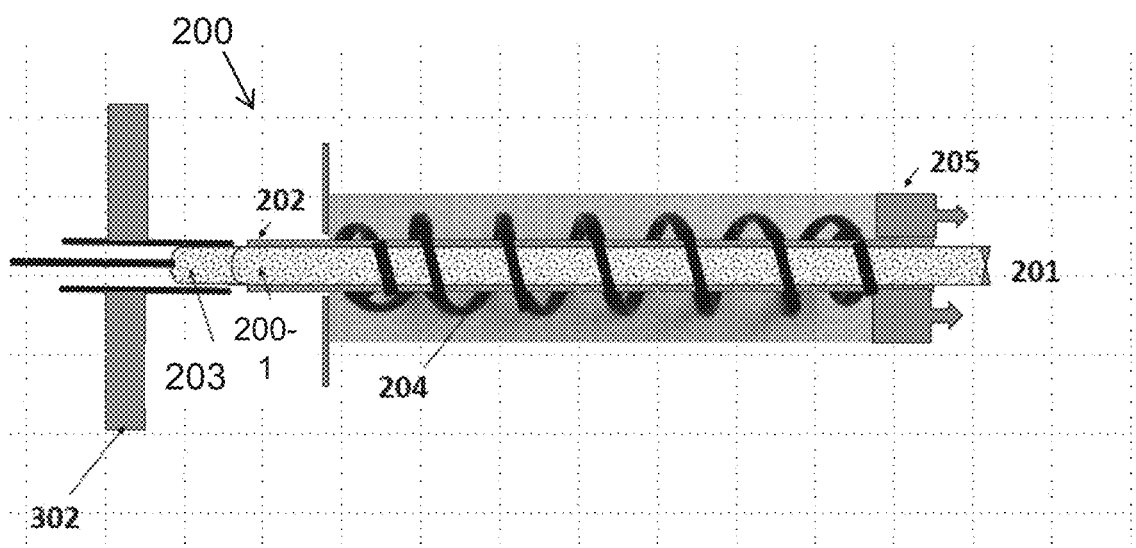
FIG. 5 schematically illustrates embodiments of an electrode device comprising or being connected to a handle.

FIG. 5 schematically illustrates a handle 302 connected to the electrode device 200 or comprised in the electrode device 200.

The impedance is a complex quantity $Z={}^{Re}Z+{}^{Im}Z$, where $^{Im}Z$ is the imaginary value of the impedance Z and $^{Re}Z$ is the real value of the impedance Z. By means of the impedance recording module 108 the conductance and the phase angle $\theta=\text{arctg}(^{Im}Z/^{Re}Z)$ between the electrode 200-1 and the reference electrode 205 may be measured or determined for a number of different frequencies of an alternating current causing the electric field between the electrodes 200-1, 205. Some examples of such frequencies are 1; 2; 4; 8; 18; and 32 kHz.

As previously mentioned, the conductance, i.e. the AC conductance, is equal to the inverse of the impedance Z. Thus, the conductance is 1/Z. Further, the phase angle θ may be expressed as $\theta=\text{arctg}(^{Im}Z/^{Re}Z)$ since loss (tangent)=1/(tan $\theta)={}^{Re}Z/^{Im}Z$.

The reason for determining the conductance and the phase angle for a number of different frequencies is to obtain conductance values, e.g. AC-conductance values, and phase angles or loss (tangent) values for different frequencies which values are representative of a specific tissue, as will be described below.

Figures 6A, 6B:
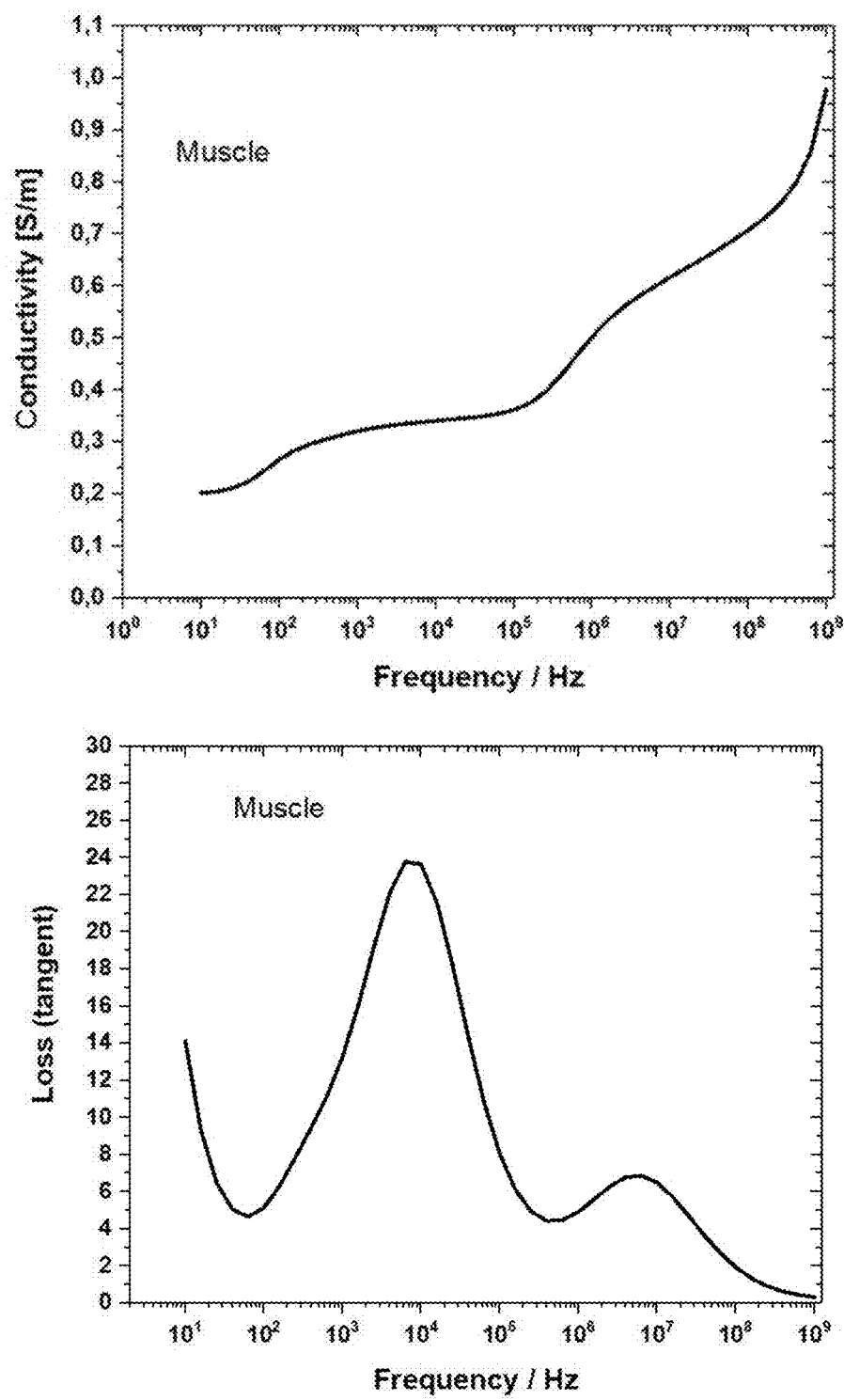
FIGS. 6A and 6B schematically illustrate how the conductance and the loss(tangent) vary with frequency for muscle tissue.
Figures 7A, 7B:
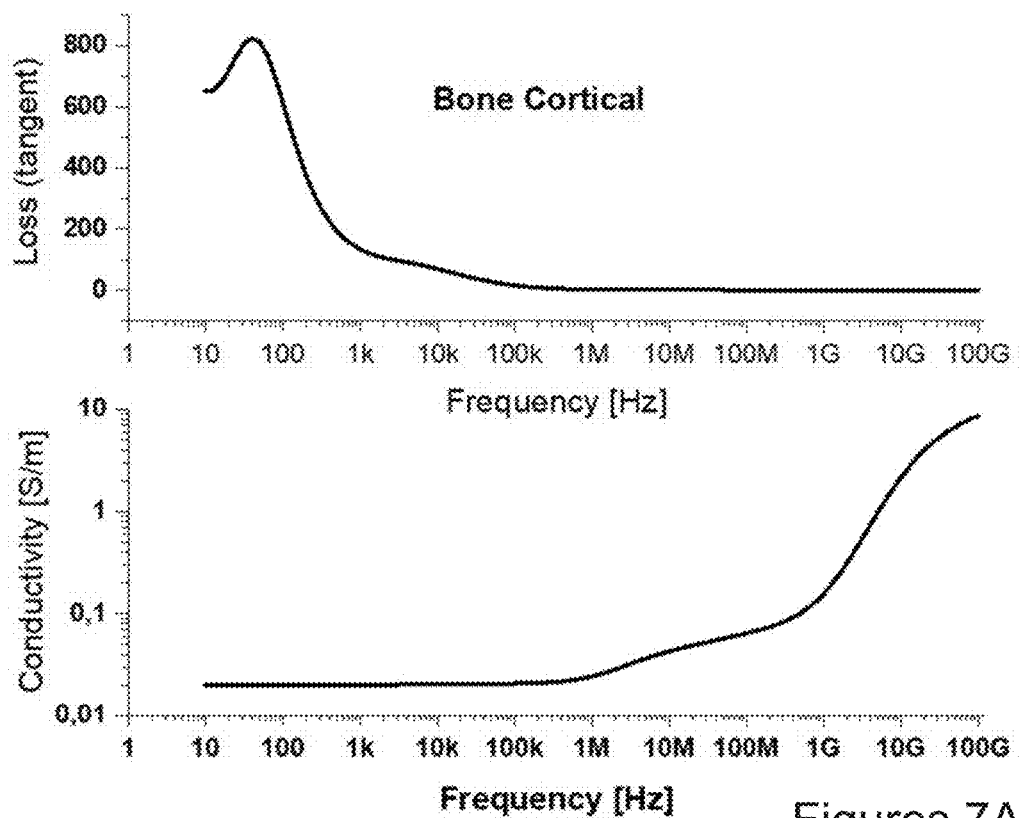
FIGS. 7A and 7B schematically illustrate how the conductance and the loss(tangent) vary with frequency for cortical bone.
Figures 8A, 8B:
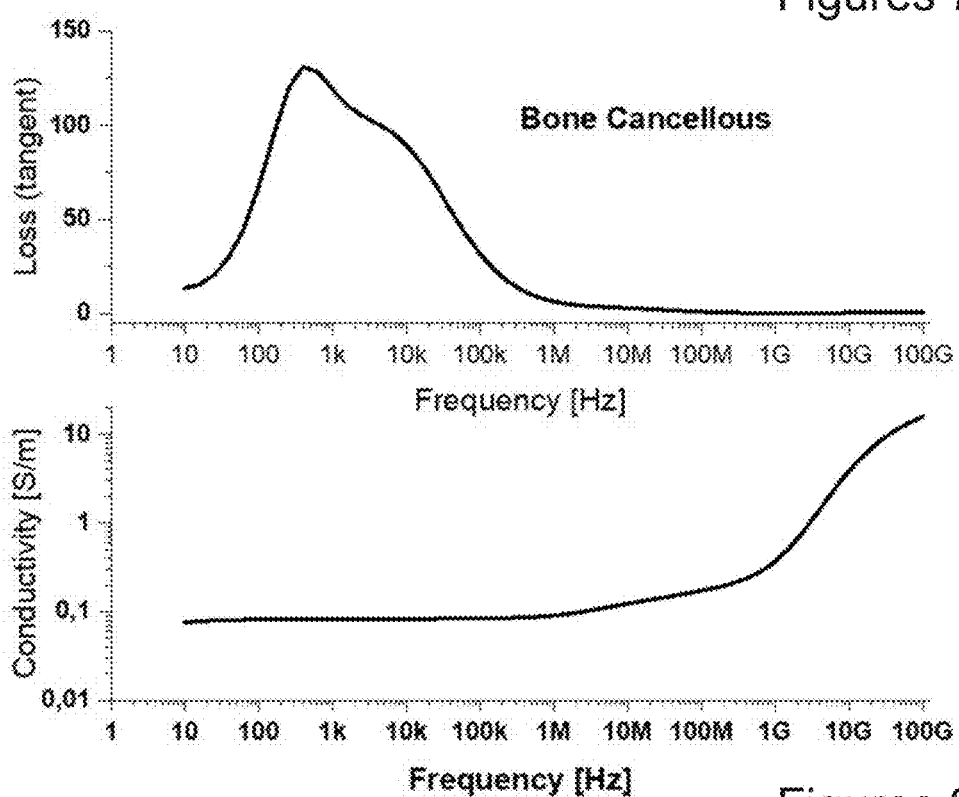
FIGS. 8A and 8B schematically illustrate how the conductance and the loss(tangent) vary with frequency for cancellous bone.
Figures 9A, 9B:
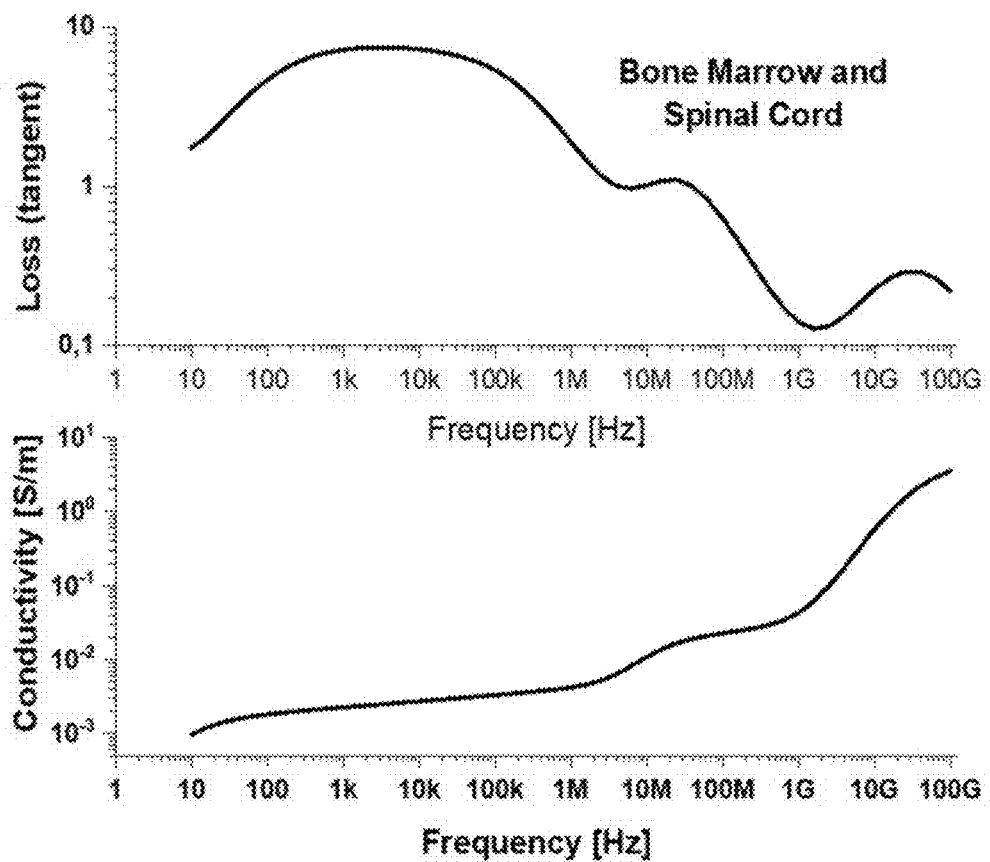
FIGS. 9A and 9B schematically illustrate how the conductance and the loss(tangent) vary with frequency for bone marrow and spinal cord.

Examples of conductivity and Loss (tangent)=|ReZ/ImZ| values versus frequency are given in FIGS. 6A and 6B, respectively, for muscle, in FIGS. 7A and 7B, respectively, for bone cortical, in FIGS. 8A and 8B, respectively, for bone cancellous, and in FIGS. 9 and 9B, respectively, for bone marrow and spinal cord. Thus, based on a number of conductance values and phase angles/loss (tangent) values determined for different frequencies, the corresponding tissue may be determined. In the FIGS. 6A-9B, the conductance and the loss (tangent) values for the different tissues are given for frequencies between 10 Hz and 100 GHz.

The Loss decreases=1/tan $\theta=(^{Re}Z/^{Im} Z)$ is sometimes in this disclosure referred to as loss (tangent). When the electrode 200-1 hits trabecular bone, the conductance, e.g. the AC-conductance, and the Loss decreases=1/tan $\theta=(^{Re}Z/^{Im} Z)$ at one of the specific frequencies, e.g. at 1 kHz, are used to monitor the type of tissue the electrode device 200, e.g. by means of the electrode 200-1, penetrates as a complement to diagnostic imaging, such as ultrasound imaging, Computer Tomography (CT) imaging, or Magnetic Reference Imaging (MRI). The AC-conductance increases and loss (tangent) decreases again as it penetrates the trabecular bone. When the conductance again decreases and the loss (tangent) increases, the electrode device 200, e.g. by means of the electrode 200-1, has reached the opposite wall and may be fixed in the desired position. When the electromagnet turns off, the drill grip releases the electrode 200-1 from the drill and the electrode 200-1 remains in the desired body part, e.g. the vertebra, when the drill is removed. Alternatively, when the electrode 200-1 is positioned using the manual tool, e.g. the handle 302, the operator will manually loosen the manual tool from the electrode 200-1 when it is in place.

The procedure may be repeated until the desired number of electrodes 200-1 are placed in the vertebra. In FIG. 3, two electrodes 200-1 placed in the vertebra are shown.

The one or more electrodes 200-1 are connected to the pulse generating device 100 and the impedance recording module 108 measures the conductance and the phase angle $\text{arctg}(^{Im}Z/^{Re}Z)$ between each one of the one or more electrodes 200-1 and the respective reference electrode 205.

Based on the measurements the treatment effect on the tissue of the desired body part may be analysed e.g. with multivariate methods to be correlated to parameters such as loss (tangent)=1/tan $\theta=(^{Re}Z/^{Im}Z)$, maximum and minimum voltage, maximum and minimum current, maximum and minimum number of pulses, and maximum and minimum specific absorbed energy for the treatment may be determined in order to achieve information about the optimal treatment conditions. For example, a tissue having a high conductance requires electric pulses having a lower voltage than a tissue having a low conductance. In correspondence, when the conductance of the tissue is high, the current is also high, and thus at a given voltage the current is higher in a tissue having a high conductance than a tissue having a low conductance.

The maximum and minimum voltage, e.g. the maximum and minimum Root Mean Square (RMS) voltage, may be determined as 1000 V and 25 V, respectively, the maximum and minimum current may be determined as 16 A and 0.2 A, respectively, the maximum and minimum number of pulses may be determined as 12 and 1, respectively, and the maximum and minimum specific absorbed energy for the treatment may be determined as 10 J/g and 2 J/g, respectively, based on the measured conductance and the phase angle.

Based on a determined current, the current density may be determined since the current density is the electric current per unit area of cross section between the electrodes.

The specific absorbed energy $_sW$ or electric dose $_sW_p$ per pulse may be calculated from the following expression:

$$_sW_p = \frac{\sigma_p \cdot E_p^2}{\rho} \cdot t_p [J \cdot kg^{-1}]$$

For a pulse train of N pulses the sum of the specific absorbed energy is as follow $$_sW = \sum_N \frac{\sigma_p \cdot E^2}{\rho} \cdot t_p [J \cdot kg^{-1}]$$

wherein $\sigma$ is the tissue conductivity for the tissue [S/m], E is the electric field strength [V/m], $t_p$ is the pulse length [s], N is the number of applied pulses, and $\rho$ is the density of tissue (e.g. muscle 1060 kg/m³).

The conductivity of the tissue after application of the electric pulses, e.g. after electroporation, $\sigma_{after}$, may be predicted by the equation $$\sigma_{after} = \sigma_{before} \cdot G_{after}/G_{before}$$

wherein $G=1/R[\Omega^{-1}$, or $S]$ is the conductance values recorded by the device 1 at one or more frequencies e.g. at one or more frequencies in the range of 2-5 kHz.

Alternatively, the conductivity of the tissue after the application of the electric pulses, e.g. after the electroporation, $\sigma_{after}$, may be predicted by the equation:

$$\sigma_{after} = \sigma_{before} \cdot tg\theta_{after}/tg\theta_{before}$$

wherein $tg\theta = tan(\theta)$ and $\theta$ is the phase angle determined before and after the application of the electric pulses.

Some Second Exemplifying Embodiments

Figure 10:
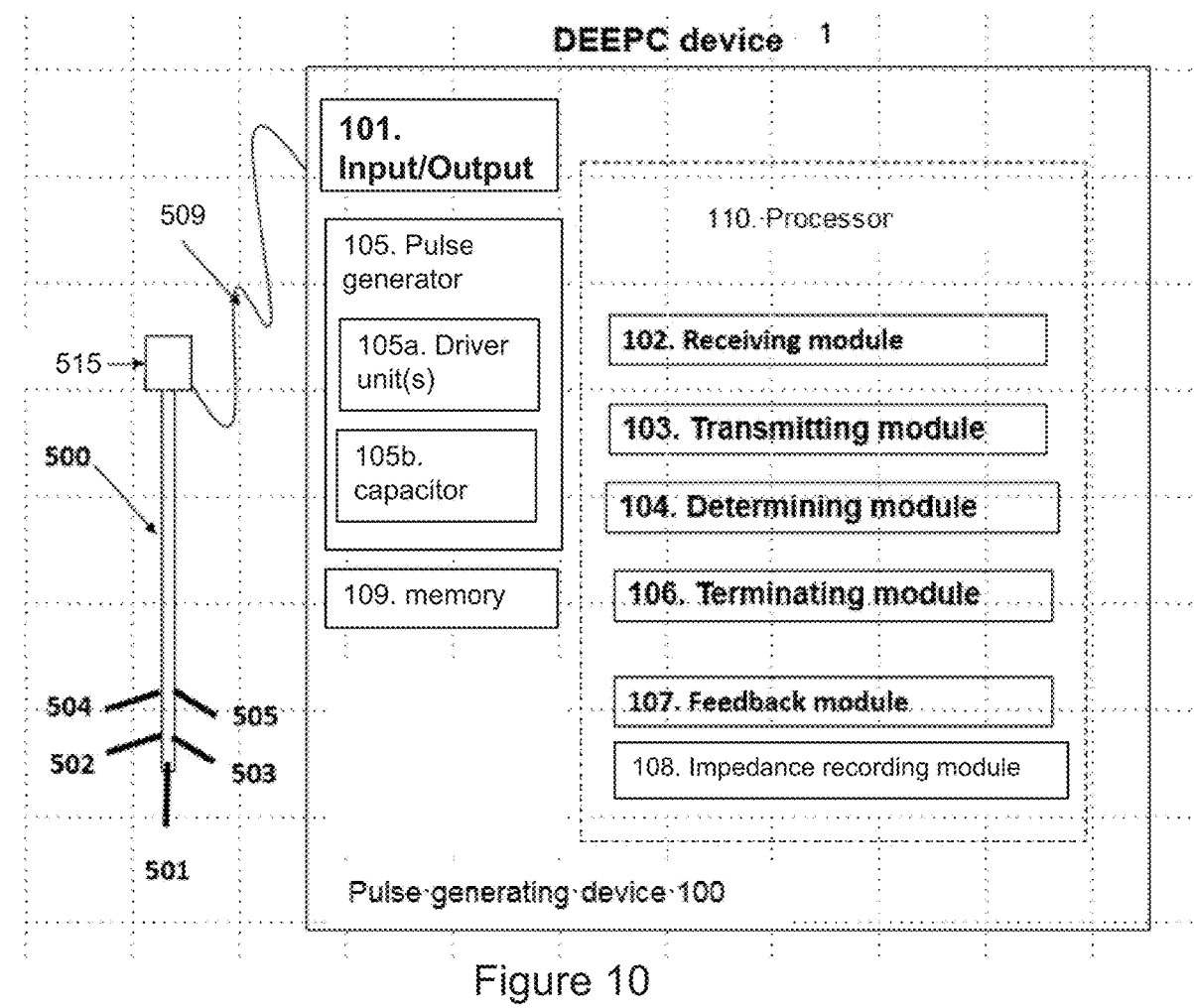
FIG. 10 schematically illustrates some second embodiments of a DEEPC device.

In some second embodiments, e.g. as schematically illustrated in the FIG. 10, the electrode device 500 is a multi-electrode device 500 comprising a plurality of electrodes 501, 502, 503, 504, 505. The number of electrodes may vary, but in some embodiments the multi-electrode device 500 comprises at least three electrodes, e.g. a first, a second and a third electrode 501, 502, 503. The multi-electrode device 500 is releasable arranged to the pulse generating device 100.

The DEEPC device 1 may be an integrated treatment unit comprising the multi-electrode device 500 connected to the pulse generating device 100 by means of cabling 509 connected to a connector 515. As schematically illustrated in FIG. 10, the pulse generating device 100 comprises an impedance recording unit 108 and a pulse generator 105 controlled by a processor 110. As previously mentioned, some exemplifying embodiments of the pulse generating device 100 will be described in more detail below.

Figure 11:
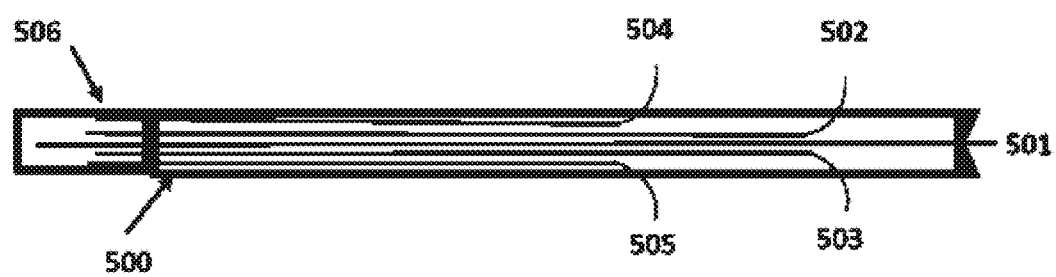
FIG. 11 schematically illustrates embodiments of a multi-electrode device.

FIG. 11 schematically illustrates some embodiments of a multi-electrode device 500. The multi-electrode unit 500 comprises a hollow tube 506, e.g. a hollow steel tube, with an insulating casing (e.g. a Teflon casing) except at the ends, wherein one of the ends, e.g. a front end, is provided with a tip having a double cut. The tube 506 may function as a drill and the double cut may provide a cutting edge. In FIG. 10, the tube 506 encloses five electrodes 501-505 of which at least two electrodes, e.g. a second and a third electrode 502, 503, end on a respective side wall of the tube. Sometimes in this disclosure the tube 506 is referred to as an electrode assembly, and it should be understood that the terms may be used interchangeably. In some embodiments, the second and third electrodes 502, 503 ends approximately 1 cm from the tip. Further, in some embodiments, a fourth and a fifth electrode 504, 505 end on a respective side wall of the tube 506, e.g. approximately 1 cm above the second and third electrodes 502, 503, and thus approximately 2 cm from the tip. The second, third, fourth and fifth electrodes 502-505 may extend out from the hollow tube through a respective opening in the side wall of the tube. The first electrode 501 may extend out from the tube through an opening in the tip. It should be understood that one or more additional electrode pairs may be added as needed.

Figure 12:
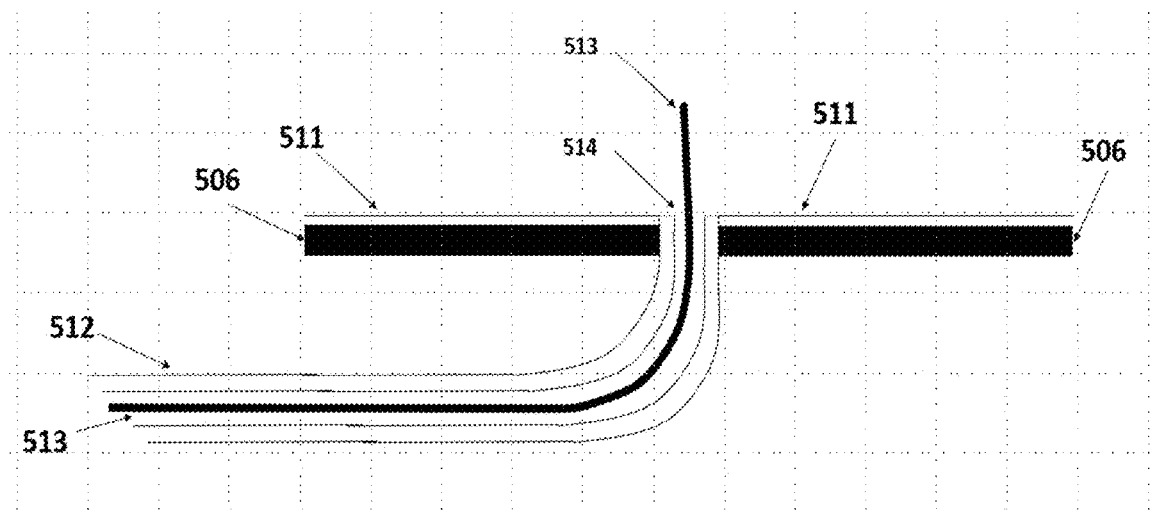
FIG. 12 schematically illustrates a part of a longitudinal cross-section of a multi-electrode device having an electrode extending out through a side hole.

FIG. 12 schematically illustrates one of the second to fifth electrodes 502-505 shown as an electrode 513. The electrode 513 is enclosed in a tube, e.g. an individual tube, 512, e.g. a Teflon tube, which opens through holes 514 on the sides of electrode assembly 506. The electrode assembly 506 may be covered with a layer 511 of Teflon.

Figure 13:
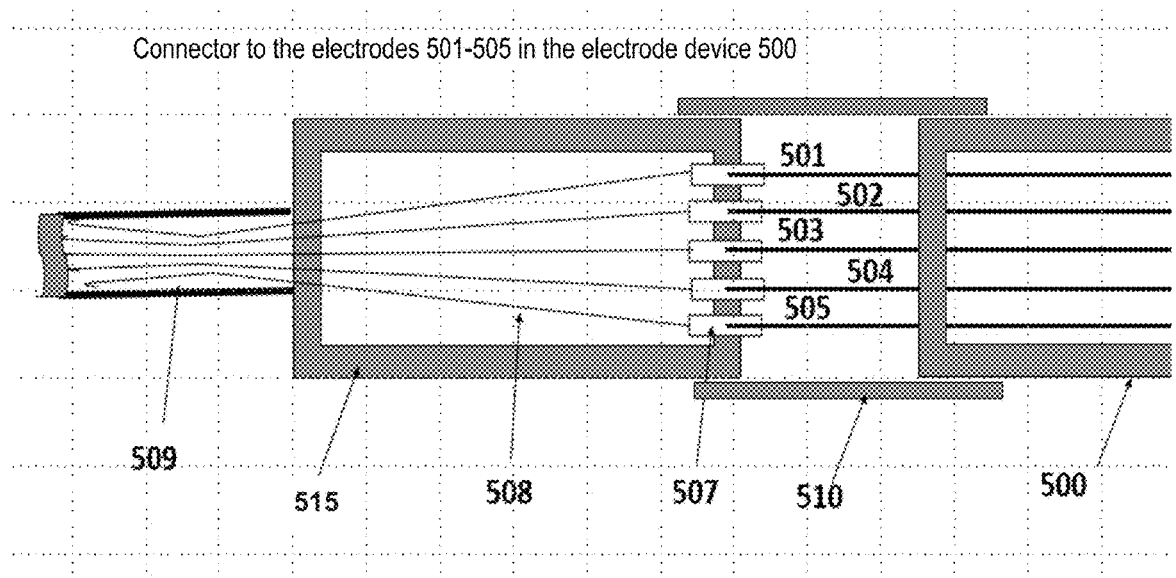
FIG. 13 schematically illustrates embodiments of a connector connecting the electrodes of an electrode device.

FIG. 13 schematically illustrates embodiments of a connector 515 to the electrodes 501-505 in the electrode device 500. The individual electrodes 501-505 are connected to the connector 515, e.g. a square connector, which, with the cable 509, is in contact with the pulse generating device 100 and thus also to the impedance recording module 108.

As illustrated in FIG. 13, the connector 515 comprises a respective stick connector 507 for connecting the respective electrode 501-505 to a respective lead 508 of the cable 509. Further, a connector 510 is configured to connect the electrode device 500 to the connector 515.

Figure 14:
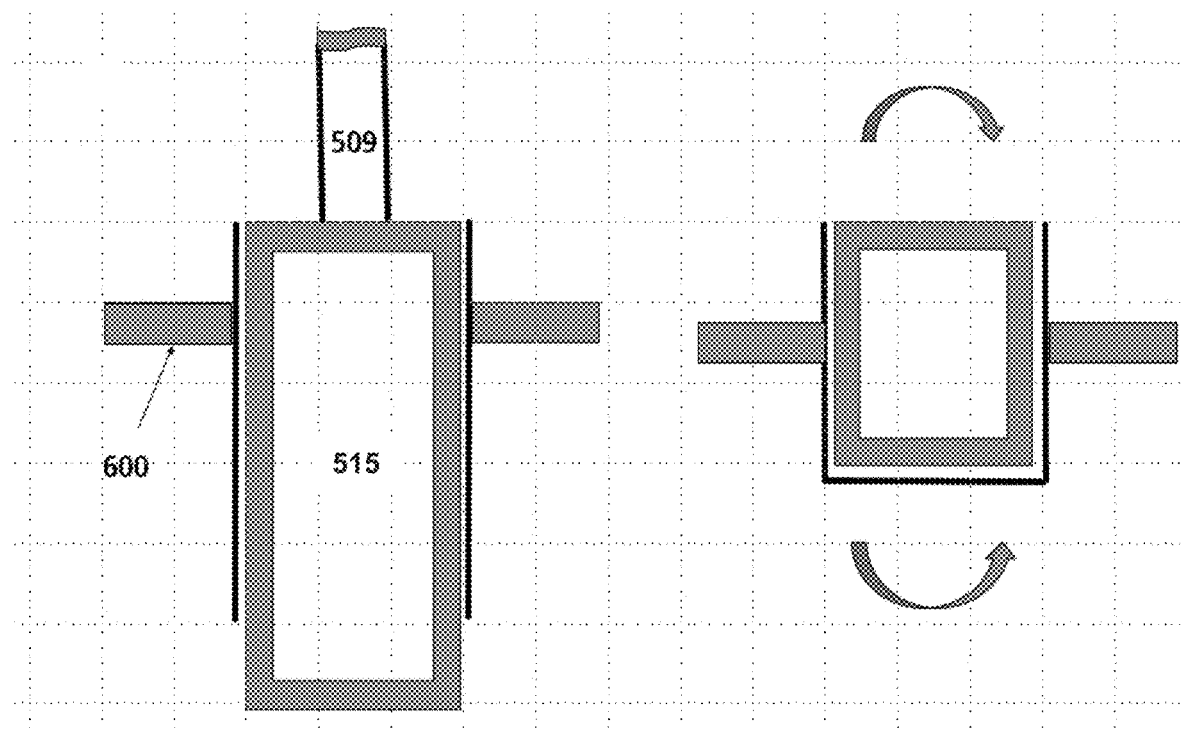
FIG. 14 schematically illustrates a hand tool connected to the connector and how it can be rotated.

As schematically illustrated in FIG. 14, a hand tool with a handle 600 may be attached to the connector 515, and with the operator's grip, the electrode device 500 alternately rotates <180 degrees back and forth so that it penetrates the intermediate tissue and the vertebra.

Figure 15:
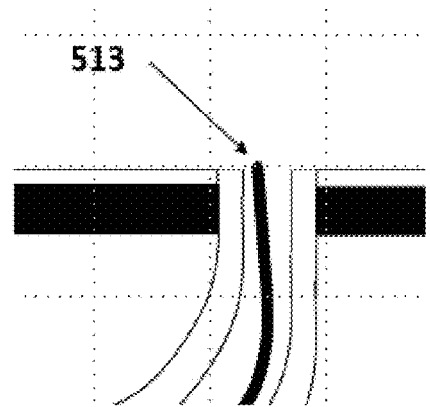
FIG. 15 schematically illustrates a part of a longitudinal cross-section of a multi-electrode device having a retracted electrode.

During penetration of intervening tissue and the skeleton, the electrodes 501-505 are retracted but may act as impedance monitor of the tissue being penetrated. A retracted electrode 513, e.g. one of the electrodes 502-505, is schematically illustrated in FIG. 15. When the electrode 513 is retracted the electrode tip fits flush or almost fits flush with the edges of the hole 514 and thus does not extend out from the hole 514 into surrounding tissue.

The impedance may be measured or determined by means of the impedance recording module 108 of the pulse generating device 100 connected to the first electrode 501 and to the reference electrodes 502 and 503. The conductance and phase angle $\theta$ are recorded between the electrodes 501-503 at a plurality of frequencies, e.g. at 1; 2; 4; 8; 18; and 32 kHz. Changes in conductance and loss (tangent)=1/ tan θ=($^{Re}Z/^{Im}Z$) at one of the specific frequencies are used to monitor which tissue the electrode assembly 506 penetrates as a complement to diagnostic imaging, such as ultrasound imaging, CT imaging, or MRI.

When the electrode assembly 506 is in place in the desired body part, e.g. the vertebra, the electrodes are advanced into the tissue through holes 514 in the side walls of the electrode assembly 506 and are connected, by means of the connector 515 and cable 509, to the pulse generating device 100. As previously mentioned, FIG. 13 schematically illustrates how the connector 515 is connected to the electrodes 501-505 in the electrode device 500.

The impedance recording module 108 may be configured to measure the conductance during the introduction of the electrode assembly 506 into the desired body part and during guidance using diagnostic imaging, such as ultrasound imaging, CT imaging, or MRI.

During the procedure for inserting the multi-electrode device 500 into the desired body part, the recorded conductance and loss (tangent) values between the electrode pair 501, 502, between the electrode pair 501, 503, and between the electrode pair 502, 503 may be displayed on a display to check the progress.

When the multi-electrode device 500, e.g. by means of the electrode assembly 506, hits trabecular (cortical) bones, the conductance and loss (tangent) values decrease between the first electrode 501 and the other electrodes 502-505, but the conductance increases and the loss (tangent) decreases again as it penetrates the trabecular bone. As the conductance tends to decrease again, the tip of the electrode assembly 506 has reached the opposite wall of the trabecular bone and the electrode assembly 506 may be fixed in the desired position. Thus, it is possible to determine the type of tissue the electrode assembly 506 penetrates by monitoring the conductance and loss(tangent) values.

The electrodes 502-505 are inserted into the desired body part to a respective desired depth and the conductance and the phase angle is recorded at a number of frequencies, e.g. 2, 4, 8, 16 and 32 kHz, in order to calculate loss(tangent) values. By means of one or more of the calculated loss (tangent) values, one or more dielectric properties of the tissue may be determined. One or more of these properties may be used for determining a suitable setting of one or more treatment parameters.

Based on the measurements, the treatment effect on the tissue of the desired body part may be analysed with multivariate methods to be correlated to parameters such as loss(tangent)=1/tan θ=($^{Re}Z/^{Im}Z$), maximum and minimum values of voltage, maximum and minimum values of current, maximum and minimum values of number of pulses, and maximum and minimum values of specific absorbed energy for the treatment may be determined in order to achieve information about the optimal treatment conditions.

As previously mentioned, the maximum and minimum voltage, e.g. the maximum and minimum RMS voltage, may be determined as 1000 V and 25 V, respectively, the maximum and minimum current may be determined as 16 A and 0.2 A, respectively, the maximum and minimum number of pulses may be determined as 12 and 1, respectively, and the maximum and minimum specific absorbed energy for the treatment may be determined as 10 J/g and 2 J/g, respectively, based on the measured conductance and the phase angle.

Some Third Exemplifying Embodiments

Figure 16:
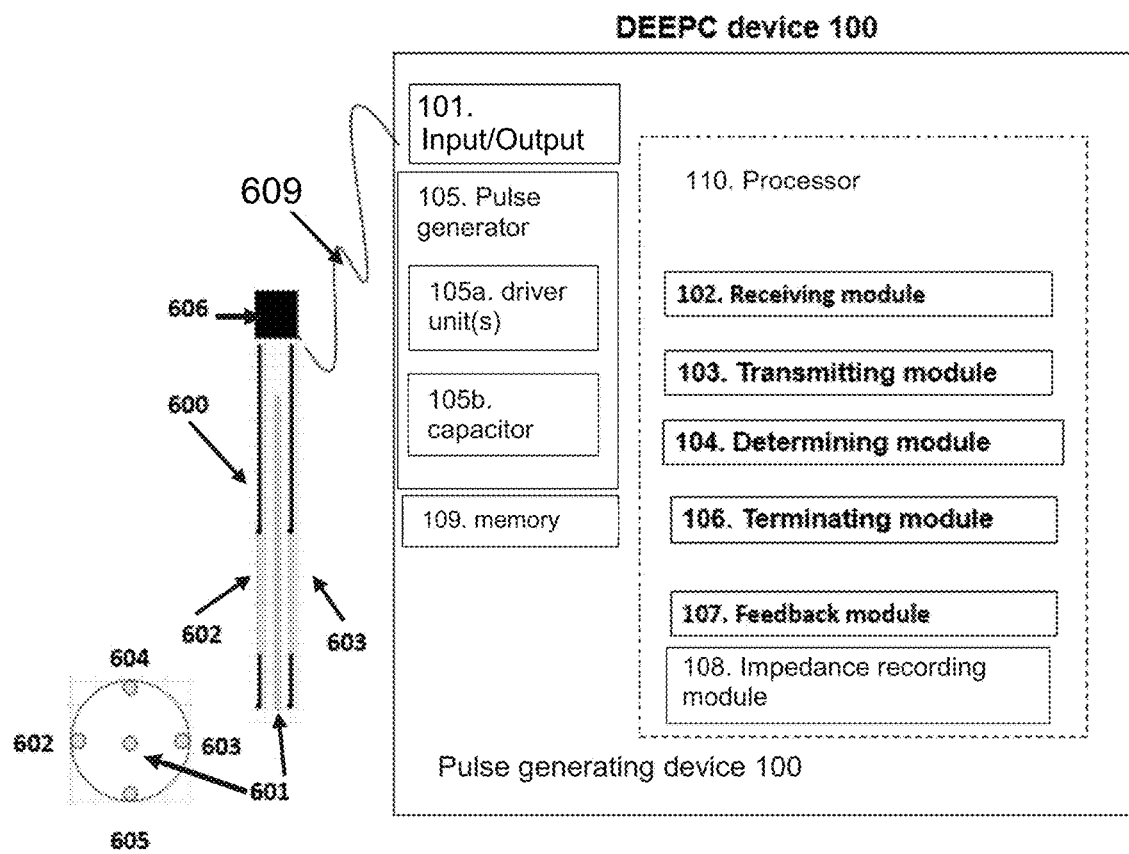
FIG. 16 schematically illustrates some third embodiments of a DEEPC device.

In some third embodiments, schematically illustrated in FIG. 16, the electrode device 600 is an expandable multi-electrode device 600 comprising a plurality of electrodes, e.g. five electrodes, 601, 602, 603, 604, 605. The number of electrodes may vary, but in some embodiments the expandable multi-electrode device 600 comprises at least three electrodes, e.g. a first, a second and a third electrode 601, 602, 603. The expandable multi-electrode device 600 is releasable arranged to the pulse generating device 100.

The DEEPC device 1 may be an integrated treatment unit comprising the expandable multi-electrode device 600 connected to the pulse generating device 100 by means of cabling 609. As illustrated in FIG. 16, the pulse generating device 100 comprises an impedance recording unit 108 and a pulse generator 105 controlled by a processor 110. As previously mentioned, some exemplifying embodiments of the pulse generating device 100 will be described in more detail below.

The expandable multi-electrode unit 600 comprises a hollow tube 600a, e.g. a hollow steel tube, with an insulating casing (e.g. a Teflon casing) except at an end, e.g. a first end or a front end. The end may comprise a tip with a double cut. The tube may function as a drill and the double cut in the tip may provide a cutting edge. In the other end, e.g. a second end opposite or almost opposite to the first end, the multi-electrode device 600 is connectable to the pulse generating device 100. The tube encloses at least five electrodes 601-605 of which at least two electrodes, e.g. a second and a third electrode 602, 603, extend along a respective side wall of the tube. The at least two electrodes, e.g. the second and third electrode 602, 603 may end on a respective side wall of the tube. In some embodiments, the second and third electrodes 602, 603 ends approximately 1 cm from the tip. In some embodiments, the electrodes 602-605 are made of thin flexible steel strips, while the central electrode 601 is a stiff needle electrode. The central electrode 601 is located centrally within the tube 600a along the longitudinal axis of the tube 600a. Further, in some embodiments, a fourth and a fifth electrode 604, 605 extend along a respective side wall of the tube. The fourth and fifth electrodes 604, 605 may end on a respective sidewall of the tube, e.g. approximately 1 cm above the second and third electrodes 602, 603, and thus approximately 2 cm from the tip. A part of the second, third, fourth and fifth electrodes 602-605 may extend out from the hollow tube through a respective opening in the side wall of the tube when for example the multi-electrode 600 is expanded. The first electrode 601 may extend out from the tube through an opening in the tip. It should be understood that one or more additional electrode pairs may be added as needed.

Figure 17:
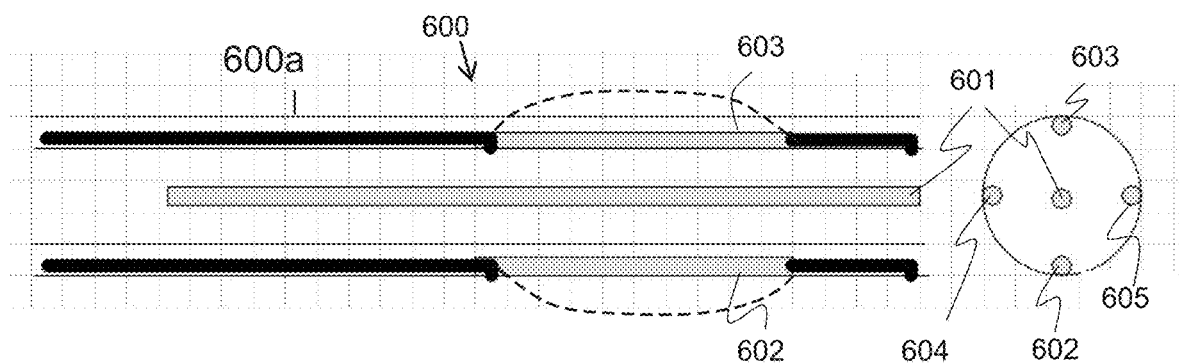
FIG. 17 schematically shows a longitudinal cross-section of an expandable multi-electrode device together with a planar front view of the expandable multi-electrode device.

A cross-sectional side view of some embodiments of the expandable multi-electrode device 600 is schematically illustrated in FIG. 17. The expansion is schematically illustrated by the dotted lines. The expansion of the expandable multi-electrode 600 may be accomplished in several ways. For example, the multi-electrode 600 may be expanded such that at least a part of the two or more side electrodes 602-605 is expanded out through the respective side opening and into the tissue to be treated by means of an expansion of a silicon balloon inside the tube.

By the expansion, the diameter of the tube 600a at the expansion volume 608 is increased as compared to the diameter of the tube 600a outside the expansion volume 608. The increased diameter provides for an improved positioning of the electrode device 600 at the desired body part preventing the electrode device 600 from being moved further into the desired body part or from being moved out from the body part.

Figure 18:
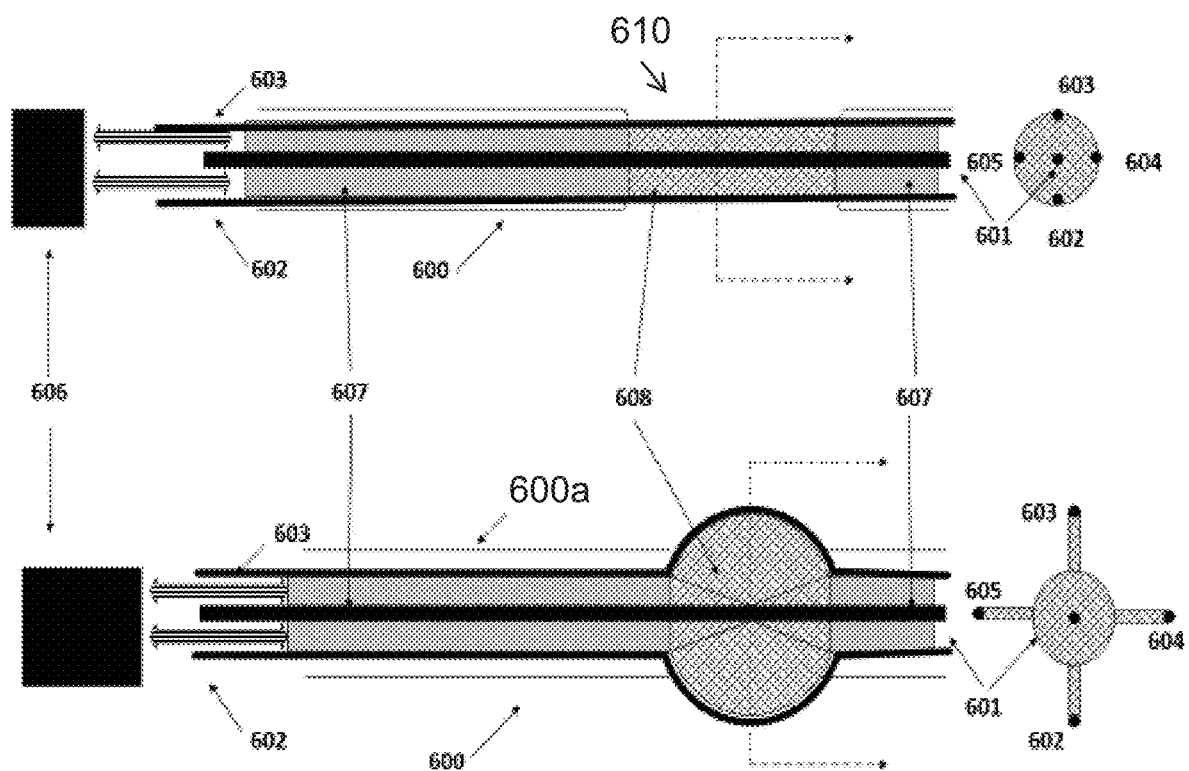
FIG. 18 schematically shows a longitudinal cross-section of an expandable multi-electrode device together with a planar front view of the expandable multi-electrode device in a non-expanded state and in an expanded state, respectively.

In some embodiments, e.g. as schematically illustrated in FIG. 18, an expansion volume 608 is filled with a compressible silicone-gel surrounded by one or more plugs 607, e.g. by Teflon plugs 607. The plug at the tip may be fixed and the plug of the electrodes and the plug above may be movable to compress the silicone gel as shown in the lower drawing of FIG. 18 thereby pushing the electrodes 602, 603, 604, and 605 outwards into the tissue. Also the central electrode 601 is pushed forward into the tissue. The excitation of the electrodes is performed by alternating the polarity between the electrode 601 and the other electrodes 602-603, and between the electrodes 602-603 pairwise and opposite in order to achieve a homogeneous treatment volume. When the expansion volume is expanded, the distance, e.g. the perpendicular distance, between the central electrode 601 and each one of the one or more other electrodes 602-605 will be increased in the area of the expanded expansion volume as compared to the case without expansion of the expansion volume. Thus, by controlling the expansion of the expansion volume 608 also the distance between the central electrode 601 and each one of the one or more other electrodes 602-605 can be controlled.

As schematically illustrated in FIG. 18, the expandable multi-electrode device 600 comprises a plurality of longitudinal side openings, e.g. at least one side opening 610, allowing the side electrodes 602-605 to expand the multi-electrode 600.

The impedance may be measured by means of the impedance recording module 108 of the pulse generating device 100 connected to the first electrode 601 and to the reference electrodes 602 and 603. The conductance and phase angle θ are recorded between the electrodes 601-603 at a plurality of frequencies, e.g. at 1; 2; 4; 8; 18; and 32 kHz. Changes in conductance and loss(tangent)=1/tan θ=($^{Re}Z/^{Im}Z$) at one of the specific frequencies are used to monitor which tissue the electrodes penetrates as a complement to diagnostic imaging, such as ultrasound imaging, CT imaging, or MRI.

When the electrodes is in place in the desired body part, e.g. the vertebra, the side electrodes 602-605 expand the multi-electrode 600 and parts of the side electrodes 602-605 extend out from the side openings into the desired body part. Further, the multi-electrode 600 is connected, by means of a connector 606 and cable 609, to the pulse generating device 100. According to embodiments described herein the electrode device may have various configurations. For example, the electrode device may comprise a single pin electrode with pad electrodes on the surface or multiple pin electrodes for large target volumes.

Some Exemplifying Embodiments of the Pulse Generating Device 100

Figure 19:
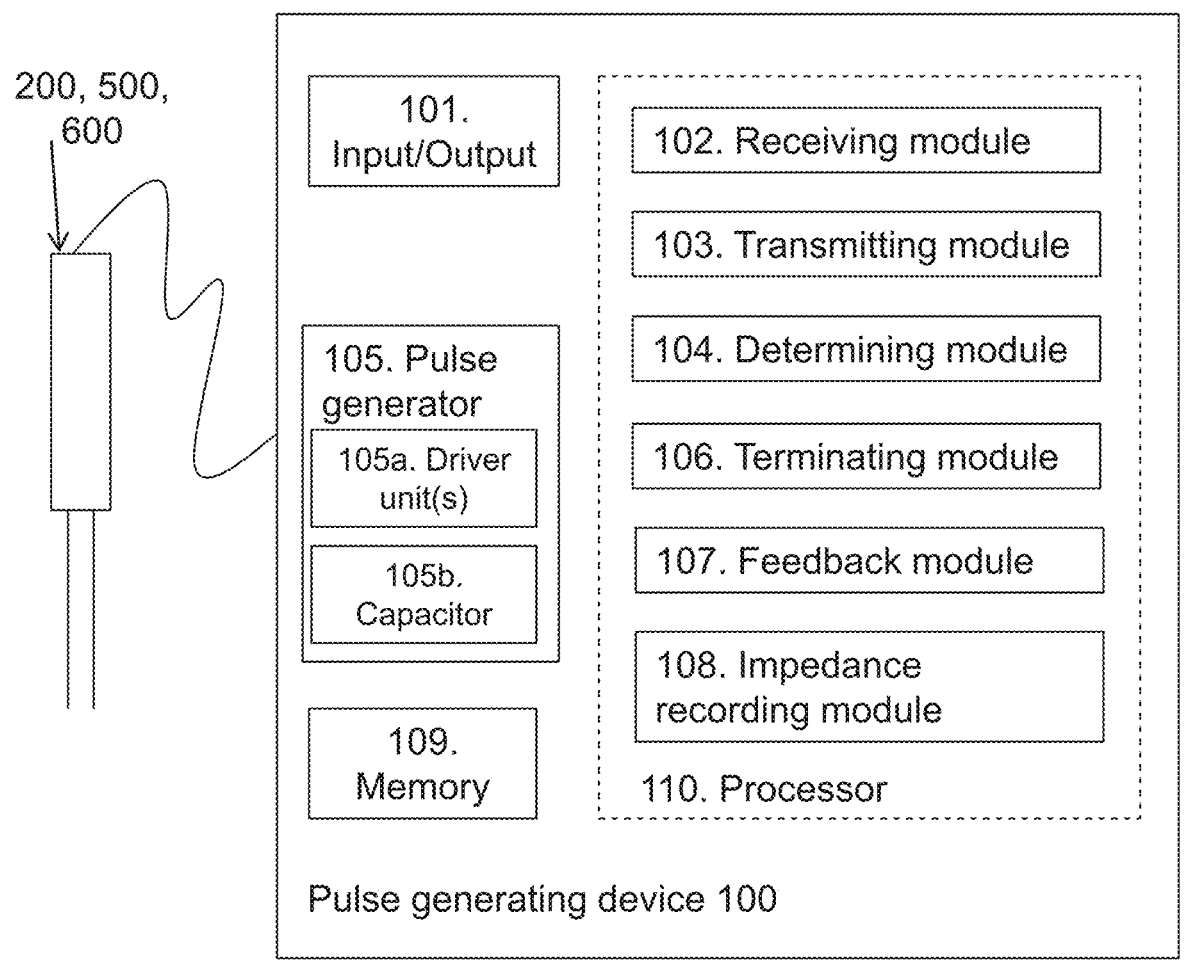
FIG. 19 schematically illustrates embodiments of a pulse generating device connected to an electrode device.

As schematically illustrated in FIG. 19, the pulse generating device 100 may comprise an input/output interface 101, to facilitate communications with a user such as an operator of the pulse generating device 100. The interface may, for example, comprise an output device such as a monitor e.g. a display device, an input device such as a keyboard, keypad, a mouse, or a combined input and output device such as a touch screen. The input and output interface 101 may additionally or alternatively comprise means for wired or wireless communication with another device (not shown).

The pulse generating device 100 may be configured to receive, by means of a receiving module 102 configured to receive, information or data from one or more other devices. The receiving module 102 may be implemented by or arranged in communication with a processor 110 of the pulse generating device 100.

The pulse generating device 100 may be configured to transmit, by means of a transmitting module 103 configured to transmit, information or data to one or more other devices. The transmitting module 103 may be implemented by or arranged in communication with the processor 110 of the pulse generating device 100.

The pulse generating device 100 may be configured to, e.g. by means of a determining module 104 configured to, determine a voltage amplitude of an electrical pulse to be generated between the at least two electrodes of the electrode device 200, 500, 600, and to determine a number of consecutive electrical pulses to be generated. The determining module 104 may be implemented by or arranged in communication with the processor 110 of the pulse generating device 100.

The pulse generating device 100 may further be configured to, e.g. by means of the determining module 104, to determine a pulse shape of the electrical pulses to be generated, and/or a pause period e.g. a time period during which the generation of pulses is to be paused and thus during which time period no pulses is to be generated.

The pulse generating device 100 may be configured to, e.g. by means of a pulse generator 105 configured to, generate one or more electrical pulses. The pulse generator 105 may be arranged in communication with the processor 110 of the pulse generating device 100.

The pulse generating device 100, e.g. by means of the pulse generator 105, is arranged in electrical communication with the at least two electrodes of the electrode device 200, 500, 600 and configured to generate one or more of the determined, e.g. predetermined, number of consecutive electrical pulses such that the generated first electrical pulse has the first voltage amplitude and that the one or more generated consecutive electrical pulses have a respective voltage amplitude consecutively decreasing between consecutively generated electrical pulses. Thereby, an increase in a current value of the one or more generated consecutive electrical pulses above a threshold value is avoided.

In some embodiments, the pulse generating device 100, e.g. by means of the pulse generator 105, is configured to generate the one or more of the determined number of consecutive electrical pulses with a respective voltage amplitude that is decreasing with a pre-set amplitude value between two consecutive electrical pulses, wherein the pre-set amplitude value is in the range of 400-1200 V. However, in some embodiments, the pre-set amplitude value is in the range of 100-1200 V.

The pulse generating device 100, e.g. by means of the pulse generator 105, may be configured to generate the one or more of the determined number of consecutive electrical pulses with a respective voltage amplitude that is exponentially decreasing between two consecutive electrical pulses. For example, the respective voltage amplitude may be exponentially decreasing between two generated consecutive electrical pulses as a function of $e^{-f_c \cdot t}$, wherein $f_c = \sigma/C$, σ is the conductivity of the desired tissue, C is the capacitance of a capacitor of the pulse generator 105, and t is the time between the two generated consecutive electrical pulses.

In some embodiments, the pulse generating device 100, e.g. by means of the pulse generator 105, is configured to first excite a first one of the at least two electrodes of the electrode device 200, 500, 600 with a positive voltage and a second one of the at least two electrodes with zero voltage.

The pulse generator 105 may then in a second excitation excite the second one of the at least two electrodes of the electrode device 200, 500, 600 with the positive voltage and the first one of the two electrodes with zero voltage. Thereby, an improved homogeneity of the therapeutic effect in the target volume is achieved. It should be that in a third excitation the pulse generator 105 may excite the first one of the at least two electrodes of the electrode device 200, 500, 600 with a positive voltage and the second one of the at least two electrodes of the electrode device 200, 500, 600 with zero voltage, and this may be repeated for every following excitation. It should be understood that each excitation corresponds to one generated pulse.

In some embodiments, the pulse generating module 105 is configured to generate modulated AC-pulses with frequency components in the range of 1 kHz to 1000 kHz, for example in the range of 20 kHz to 200 kHz.

One or more driver units 105a may be comprised in or connected to the pulse generator 105. Each of the one or more driver units 105a may be configured to generate an electrical pulse between a pair of electrodes of the electrode device 200, 500, 600. Thus, in case of several pairs of electrodes, the pulse generator 105 may comprise a driver unit 105a for each pair of electrodes, and consequently the number of driver units 105a corresponds to the number of pairs of electrodes. However, it should be understood that the number of driver units 105a may be less than or more than the number of electrode pairs.

One or more capacitors 105b may be comprised in or connected to the pulse generator 105. Each one of the one or more capacitors 105b may be charged to a desired voltage value, e.g. the pre-set voltage value, and configured to be discharged to create one or more electrical pulses. For example, the capacitor 105b may be configured to be discharged stepwise to create a pulse The pulse generating device 100 may be configured to, e.g. by means of a terminating module 106 configured to, terminate generation of one or more electrical pulses. The terminating module 106 may be implemented by or arranged in communication with the processor 110 of the pulse generating device 100.

The pulse generating device 100, e.g. by means of the terminating module 106, may be configured to terminate generation of the one or more of the determined number of electrical pulses when a value of a total absorbed energy, caused in the desired tissue by the one or more generated electrical pulses, exceeds a desired threshold value.

In some embodiments, the absorbed energy is a specific absorbed energy, e.g. an absorbed energy value given per kilogram.

The pulse generating device 100, e.g. by means of the terminating module 106, may further be configured to terminate generation of the one or more of the determined number of electrical pulses when one of the respective current values of the generated electrical pulses is outside the desired current interval.

The pulse generating device 100 is configured to, e.g. by means of a feedback module 107 configured to, give feedback relating to one or more generated electrical pulses. The feedback module 107 may be implemented by or arranged in communication with the processor 110 of the pulse generating device 100.

In some embodiments, the pulse generating device 100, e.g. by means of the feedback module 107, is configured to determine a respective absorbed energy of each one of the one or more generated electrical pulses and to send information relating to the determined respective absorbed energy, and possibly the respective generated electrical pulse, to the terminating module 106.

The pulse generating device 100 may be configured to, e.g. by means of an impedance recording module 108 configured to, record, e.g. measure, the current of a pulse, e.g. the current of a generated pulse. The impedance recording module 108 may be implemented by or arranged in communication with the processor 110 of the pulse generating device 100.

For ablation purpose it may be desirable to control the time period to reach the ablation temperature by feedback control of power delivered by the electric pulses to the desired tissue. Feedback control may be performed by tissue temperature recording with one or more thermistor probes or thermo-elements (not shown) inserted in the target area.

The pulse generating device 100 may also comprise or be connected to means for storing data. In some embodiments, the pulse generating device 100 may further comprise or be connected to a memory 109 configured to store the data relating to the delivery of electrical pulses to the desired tissue of the mammal. The data may be processed or non-processed data and/or information relating thereto. The memory 109 may comprise one or more memory units. Further, the memory 109 may be a computer data storage or a semiconductor memory such as a computer memory, a read-only memory, a volatile memory or a non-volatile memory. The memory 109 is arranged to be used to store obtained information, data, configurations, and applications to perform the methods herein when being executed in the pulse generating device 100.

Embodiments herein for delivery of electrical pulses to the desired tissue of the mammal may be implemented through one or more processors, such as the processor 110 in the arrangement depicted in some of the figures above, together with computer program code for performing the functions and/or method actions of embodiments herein. The program code mentioned above may also be provided as a computer program product, for instance in the form of a data carrier carrying computer program code for performing the embodiments herein when being loaded into the pulse generating device 100. One such carrier may be in the form of an electronic signal, an optical signal, a radio signal or a computer readable storage medium. The computer readable storage medium may be a CD ROM disc, SIM card or a memory stick.

The computer program code may furthermore be provided as program code stored on a server and downloaded to the pulse generating device 100.

Those skilled in the art will also appreciate that the input/output interface 101, the receiving module 102, the transmitting module 103, the determining module 104, the pulse generator 105, the terminating module 106, the feedback module 107, and the impedance recording module 108 above may refer to a combination of analogue and digital circuits, and/or one or more processors configured with software and/or firmware, e.g. stored in the memory 109, that when executed by the one or more processors such as the processors in the pulse generating device 100 perform as described above. One or more of these processors, as well as the other digital hardware, may be included in a single Application-Specific Integrated Circuitry (ASIC), or several processors and various digital hardware may be distributed among several separate components, whether individually packaged or assembled into a System-on-a-Chip (SoC).

When the word "comprise" or "comprising" is used in this disclosure it shall be interpreted as non-limiting, i.e. meaning "consist at least of".

Modifications and other variants of the described embodiment(s) will come to mind to one skilled in the art having the benefit of teachings presented in the foregoing descriptions and the associated drawings. Therefore, it is to be understood that the embodiment(s) herein is/are not be limited to the specific examples disclosed and that modifications and other variants are intended to be included within the scope of this disclosure. Although specific terms may be employed herein, they are used in a generic and descriptive sense only and not for purposes of limitation.

The invention claimed is:

1. A dynamic electro-enhanced pain control device for delivery of electrical pulses to a desired tissue of a mammal in dynamic electro-enhanced pain control therapy, the dynamic electro-enhanced pain control device comprises: (a) a pulse generating device comprising an impedance recording unit and a pulse generator controlled by a processor, and (b) an electrode device connected to the pulse generating device, wherein:

the pulse generating device, by means of the impedance recording unit and the processor, is configured to determine conductance and phase angle values between an electrode of the electrode device and a reference electrode of the electrode device when the electrode device is inserted into a desired body part comprising the desired tissue and when pulses based on alternating currents having different frequencies are generated, by the pulse generator, to the desired body part between the electrode and the reference electrode;

based on the determined conductance and phase angle values, the pulse generating device is configured to determine a type of tissue the electrode device penetrates, when the electrode device is inserted into the desired body part;

based on the determined conductance and phase angle values, the pulse generating device is configured to determine one or more parameters of electrical pulses to be delivered to the desired tissue, when the electrode device is arranged at the desired tissue; and the pulse generator is configured to generate the electrical pulses having the determined one or more parameters, wherein the pulse generating device is configured to determine one or more parameters of electrical pulses as one or more of:

a maximum voltage as 1000 V;
a minimum voltage as 25 V;
a maximum current as 16 A;
a minimum current as 0.2 A;
a maximum number of pulses as 12;
a minimum number of pulses as 1;
a maximum specific absorbed energy as 10 J/g; and
a minimum specific absorbed energy as 2 J/g.

2. The device of claim 1, wherein the pulse generating device is configured to determine conductance and phase angle values at a number of different frequencies and wherein the pulse generating device is configured to determine the type of tissue based on how the determined conductance and phase angle values change with changing frequencies.

3. The device of claim 1, wherein the pulse generating device is configured to determine conductance and phase angle values at a number of different frequencies and wherein the pulse generating device is configured to determine the type of tissue based on how a ratio of the determined phase angle value to the determined conductance value change with changing frequencies.

4. The device of claim 1, wherein the pulse generating device is configured to generate electrical pulses based on alternating currents having frequencies in a range of 1 kHz to 1000 kHz.

5. A dynamic electro-enhanced pain control device for delivery of electrical pulses to a desired tissue of a mammal in dynamic electro-enhanced pain control therapy, the dynamic electro-enhanced pain control device comprises (a) a pulse generating device comprising an impedance recording unit and a pulse generator controlled by a processor, and (b) an electrode device connected to the pulse generating device, wherein:

the pulse generating device, by means of the impedance recording unit and the processor, is configured to determine conductance and phase angle values between an electrode of the electrode device and a reference electrode of the electrode device when the electrode device is inserted into a desired body part comprising the desired tissue and when pulses based on alternating currents having different frequencies are generated, by the pulse generator, to the desired body part between the electrode and the reference electrode;

based on the determined conductance and phase angle values, the pulse generating device is configured to determine a type of tissue the electrode device penetrates, when the electrode device is inserted into the desired body part;

based on the determined conductance and phase angle values, the pulse generating device is configured to determine one or more parameters of electrical pulses to be delivered to the desired tissue, when the electrode device is arranged at the desired tissue; and in that the pulse generator is configured to generate the electrical pulses having the determined one or more parameters, The device of claim 1, wherein the electrode device comprises:

one or more needle electrode comprising an elongated insulating cover along a longitudinal envelope surface of the one or more needle electrode, having a tip at one end thereof configured to penetrate into the desired body part, and having another end thereof configured to be connected to the pulse generating device; and the reference electrode being a sliding reference electrode surrounding the needle electrode with a spring and configured to push against an entrance surface of the desired body part when in use.

6. A dynamic electro-enhanced pain control device for delivery of electrical pulses to a desired tissue of a mammal in dynamic electro-enhanced pain control therapy, the dynamic electro-enhanced pain control device comprises (a) a pulse generating device comprising an impedance recording unit and a pulse generator controlled by a processor, and (b) an electrode device connected to the pulse generating device, wherein:

the pulse generating device, by means of the impedance measuring unit and the processor, is configured to determine conductance and phase angle values between an electrode of the electrode device and a reference electrode of the electrode device when the electrode device is inserted into a desired body part comprising the desired tissue and when pulses based on alternating currents having different frequencies are generated, by the pulse generator, to the desired body part between the electrode and the reference electrode;

based on the determined conductance and phase angle values, the pulse generating device is configured to determine a type of tissue the electrode device penetrates, when the electrode device is inserted into the desired body part;

based on the determined conductance and phase angle values, the pulse generating device is configured to determine one or more parameters of electrical pulses to be delivered to the desired tissue, when the electrode device is arranged at the desired tissue; and in that the pulse generator is configured to generate the electrical pulses having the determined one or more parameters, The device of claim 1, wherein the electrode device comprises:

a first tube with an insulating casing except at a front end being configured to penetrate into the desired body part, and another end thereof configured to be connected to the pulse generating device;

a first electrode configured to extend out from an opening in the front end; and one or more electrode pairs, wherein both electrodes of an electrode pair are configured to extend out from a respective opening in a side wall of the tube at a common distance from the front end, and wherein each electrode of the electrode pair is enclosed in a respective second tube which opens through the respective opening in the side wall of the first tube.

7. A dynamic electro-enhanced pain control device for delivery of electrical pulses to a desired tissue of a mammal in dynamic electro-enhanced pain control therapy, the dynamic electro-enhanced pain control device comprises (a) a pulse generating device comprising an impedance recording unit and a pulse generator controlled by a processor, and (b) an electrode device connected to the pulse generating device, wherein:

the pulse generating device, by means of the impedance measuring unit and the processor, is configured to determine conductance and phase angle values between an electrode of the electrode device and a reference electrode of the electrode device when the electrode device is inserted into a desired body part comprising the desired tissue and when pulses based on alternating currents having different frequencies are generated, by the pulse generator, to the desired body part between the electrode and the reference electrode;

based on the determined conductance and phase angle values, the pulse generating device is configured to determine a type of tissue the electrode device penetrates, when the electrode device is inserted into the desired body part;

based on the determined conductance and phase angle values, the pulse generating device is configured to determine one or more parameters of electrical pulses to be delivered to the desired tissue, when the electrode device is arranged at the desired tissue; and the pulse generator is configured to generate the electrical pulses having the determined one or more parameters, The device of claim 1, wherein the electrode device is an expandable multi-electrode device comprising:

a hollow tube with an insulating casing except at a front end being configured to penetrate into the desired body part, and having another end thereof configured to be connected to the pulse generating device;

a central stiff electrode configured to extend out from an opening in the front end;

one or more electrode pairs comprising electrodes made of flexible steel strips; and an expansion volume configured, when expanded, to push parts of electrodes of the one or more electrode pairs out through a respective opening in a side wall of the tube and to push the central stiff electrode forward through the opening in the front end, wherein a diameter of the tube at the expansion volume is increased as compared to the diameter of the tube outside the expansion volume.

8. The device of claim 1, wherein the pulse generating device is configured to determine a specific absorbed energy sW for a number N of electric pulses p as:

$$sW = \sum_N \frac{\sigma_p \cdot E^2}{\rho} \cdot t_p [J \cdot kg^{-1}]$$

wherein $\sigma_p$ is a tissue conductivity for the tissue [S/m], E is an electric field strength [V/m], $t_p$ is a pulse length [s], N is a number of applied pulses, and $\rho$ is a density of the tissue, and wherein the conductivity of the tissue after application of the electric pulses, $\sigma_{after}$, is determined as one out of:

$\sigma_{after} = \sigma_{before} \cdot G_{after}/G_{before}$, wherein $G=1/R$ [$\Omega^{-1}$, S] is the conductance; and $\sigma_{after} = \sigma_{before} \cdot tg\theta_{after}/tg\theta_{before}$, wherein $\theta$ is the phase angle.

* * * * *

UNITED STATES PATENT AND TRADEMARK OFFICE
CERTIFICATE OF CORRECTION

PATENT NO.          : 11,219,764 B2
APPLICATION NO.     : 16/633327
DATED               : January 11, 2022
INVENTOR(S)         : Mohan Frick et al.

It is certified that error appears in the above-identified patent and that said Letters Patent is hereby corrected as shown below:

In the Specification

At Column 6, Line 27, delete "$(^{Re}Z/^{Im}\,Z)$" and insert -- $(^{Re}Z/^{Im}Z)$ --.

At Column 6, Line 31, delete "$(^{Re}Z/^{Im}\,Z)$" and insert -- $(^{Re}Z/^{Im}Z)$ --.

At Column 13, Line 35, delete "pulse" and insert -- pulse. --.

In the Claims

At Column 16, Lines 5-34, in Claim 5, delete "A dynamic electro-enhanced pain control device for delivery of electrical pulses to a desired tissue of a mammal in dynamic electro-enhanced pain control therapy, the dynamic electro-enhanced pain control device comprises (a) a pulse generating device comprising an impedance recording unit and a pulse generator controlled by a processor, and (b) an electrode device connected to the pulse generating device, wherein: the pulse generating device, by means of the impedance recording unit and the processor, is configured to determine conductance and phase angle values between an electrode of the electrode device and a reference electrode of the electrode device when the electrode device is inserted into a desired body part comprising the desired tissue and when pulses based on alternating currents having different frequencies are generated, by the pulse generator, to the desired body part between the electrode and the reference electrode; based on the determined conductance and phase angle values, the pulse generating device is configured to determine a type of tissue the electrode device penetrates, when the electrode device is inserted into the desired body part; based on the determined conductance and phase angle values, the pulse generating device is configured to determine one or more parameters of electrical pulses to be delivered to the desired tissue, when the electrode device is arranged at the desired tissue; and in that the pulse generator is configured to generate the electrical pulses having the determined one or more parameters,".

At Column 16, Lines 48-67 and Column 17, Lines 1-10, in Claim 6, delete "A dynamic electro-enhanced pain control device for delivery of electrical pulses to a desired tissue of a mammal in Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*

Page 1 of 2 dynamic electro-enhanced pain control therapy, the dynamic electro-enhanced pain control device comprises (a) a pulse generating device comprising an impedance recording unit and a pulse generator controlled by a processor, and (b) an electrode device connected to the pulse generating device, wherein: the pulse generating device, by means of the impedance measuring unit and the processor, is configured to determine conductance and phase angle values between an electrode of the electrode device and a reference electrode of the electrode device when the electrode device is inserted into a desired body part comprising the desired tissue and when pulses based on alternating currents having different frequencies are generated, by the pulse generator, to the desired body part between the electrode and the reference electrode; based on the determined conductance and phase angle values, the pulse generating device is configured to determine a type of tissue the electrode device penetrates, when the electrode device is inserted into the desired body part; based on the determined conductance and phase angle values, the pulse generating device is configured to determine one or more parameters of electrical pulses to be delivered to the desired tissue, when the electrode device is arranged at the desired tissue; and in that the pulse generator is configured to generate the electrical pulses having the determined one or more parameters,".

At Column 17, Lines 26-48 and Column 18, Lines 1-7, in Claim 7, delete "A dynamic electro-enhanced pain control device for delivery of electrical pulses to a desired tissue of a mammal in dynamic electro-enhanced pain control therapy, the dynamic electro-enhanced pain control device comprises (a) a pulse generating device comprising an impedance recording unit and a pulse generator controlled by a processor, and (b) an electrode device connected to the pulse generating device, wherein: the pulse generating device, by means of the impedance measuring unit and the processor, is configured to determine conductance and phase angle values between an electrode of the electrode device and a reference electrode of the electrode device when the electrode device is inserted into a desired body part comprising the desired tissue and when pulses based on alternating currents having different frequencies are generated, by the pulse generator, to the desired body part between the electrode and the reference electrode; based on the determined conductance and phase angle values, the pulse generating device is configured to determine a type of tissue the electrode device penetrates, when the electrode device is inserted into the desired body part; based on the determined conductance and phase angle values, the pulse generating device is configured to determine one or more parameters of electrical pulses to be delivered to the desired tissue, when the electrode device is arranged at the desired tissue; and the pulse generator is configured to generate the electrical pulses having the determined one or more parameters,".

At Column 18, Line 30, in Claim 8, delete "sW" and insert -- $_sW$ --.